(12) United States Patent
Bertelsen et al.

(10) Patent No.: US 9,181,316 B2
(45) Date of Patent: *Nov. 10, 2015

(54) METHOD FOR ISOLATING OSTEOPONTIN USING FEEDS CONTAINING CMP OR CASEIN SPECIES

(75) Inventors: Hans Bertelsen, Videbaek (DK); Peter Langborg Wejse, Aarhus N (DK); Trine Trúgvason, Lem St. (DK)

(73) Assignee: ARLA FOODS AMBA (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/002,578

(22) PCT Filed: Mar. 5, 2012

(86) PCT No.: PCT/EP2012/053748
§ 371 (c)(1),
(2), (4) Date: Nov. 1, 2013

(87) PCT Pub. No.: WO2012/117119
PCT Pub. Date: Sep. 7, 2012

(65) Prior Publication Data
US 2014/0051831 A1    Feb. 20, 2014

Related U.S. Application Data

(60) Provisional application No. 61/448,775, filed on Mar. 3, 2011.

(30) Foreign Application Priority Data

Mar. 3, 2011 (EP) .................................. 11156826

(51) Int. Cl.
C07K 14/52 (2006.01)
A23J 1/20 (2006.01)
C07K 1/18 (2006.01)
C07K 14/47 (2006.01)

(52) U.S. Cl.
CPC . *C07K 14/52* (2013.01); *A23J 1/20* (2013.01); *C07K 1/18* (2013.01); *C07K 14/47* (2013.01)

(58) Field of Classification Search
None
See application file for complete search history.

(56) References Cited

U.S. PATENT DOCUMENTS 6,555,659 B1    4/2003 Ayers et al.
7,018,665 B2 *  3/2006 Ayers et al. ............... 426/334
2003/0149249 A1 8/2003 Sorensen et al.

FOREIGN PATENT DOCUMENTS

| CN | 1810292 | 8/2006 |
|---|---|---|
| WO | 99/33415 A1 | 7/1999 |
| WO | 01/49741 A1 | 7/2001 |
| WO | 02/28413 A1 | 4/2002 |
| WO | WO 02/28413 A1 | 4/2002 |

OTHER PUBLICATIONS

Fong et al., "Fractionation of bovine whey proteins and characterisation by proteomic techniques", International Dairy Journal 18 (2008) 23-46.*
Tek et al., "Effect of Conductivity, pH, and Elution Buffer Salinity on Glycomacropeptide Recovery from Whey Using Anion Exchange Chromatography", Journal of Food Science, vol. 70, Nr. 4, 2005, E295-E300.*
Abstract for CN 1810292.
U.S. Appl. No. 14/002,614, filed Nov. 1, 2013.
Cohen, Practical Organic Chemistry, 1910.
Evans et al., "Comparison of composition, sensory, and volatile components of thirty-four percent whey protein and milk serum proteins concentrates", J. Dairy Sci. 92 :4773-4791, 2009.
Scopes, "Protein Purification: Principles and Practice"; 3rd ed., Springer Verlag New York, Inc., pp. 103-106 and title page ISBN 0-387-94072-3.
International Search Report mailed Jun. 15, 2012, for PCT/EP2012/053749.
International Preliminary Report on Patentability mailed Jul. 5, 2013, for PCT/EP2012/053748.
N. Azuma, A. Maeta, K. Fukuchi, C. Kanno, A Rapid Method for Purifying Osteopontin From Bovine Milk and Interaction Between Osteopontin and Other Milk Proteins, International Dairy Journal, Elsevier Applied Science, Barking, GB, vol. 16, No. 4, Apr. 1, 2006, pp. 370-378.
Steen Sørensen, Steen Just Justesen, and Anders H. Johnsen, Purification and Characterization of Osteopontin From Human Milk, Protein Expression and Purification, Academic Press, San Diego, Ca., vol. 30, No. 2, Aug. 1, 2003, pp. 238-245.
Kayla J. Bayless, George E. Davis, and Gerald A. Meininger, Isolation and Biological Properties of Osteopontin From Bovine Milk, Protein Expression and Purification, Academic Press, San Diego, Ca., vol. 9, No. 3, Apr. 1, 1997, pp. 309-314.

* cited by examiner

*Primary Examiner* — Suzanne M Noakes
(74) *Attorney, Agent, or Firm* — Hershkovitz & Associates, PLLC; Abe Hershkovitz; Stanislaus Aksman

(57) ABSTRACT

The present invention pertains to a method for isolating osteopontin from a milk-derived feed containing caseino macropeptide and/or free beta casein, such as e.g. a feed based on milk serum or sweet whey. Particularly, the present method involves the use of a narrow window of pH and specific conductance of the milk-derived feed, which surprisingly has proven to provide a very efficient isolation of osteopontin from chemically complex feeds.

29 Claims, 2 Drawing Sheets

METHOD FOR ISOLATING OSTEOPONTIN USING FEEDS CONTAINING CMP OR CASEIN SPECIES

CROSS-REFERENCE TO RELATED APPLICATIONS

The present Application is a U.S. National Phase of PCT/EP2012/053748 filed on Mar. 5, 2012 ("PCT Application"), which claims priority from U.S. Provisional Application No. 61/448,775 filed on Mar. 3, 2011 and European Patent Application No. EP 11156826.7, filed on Mar. 3, 2011. The PCT Application, the U.S. Provisional application and the EP Patent Application are hereby incorporated by reference in their entirety into the present Application. The PCT application, incorporated by reference herein, includes any amendments entered in the PCT application.

FIELD OF THE INVENTION

The present invention pertains to a method for isolating osteopontin from a milk-derived feed, e.g. a feed based on milk serum or sweet whey. Particularly, the present method involves the use of a narrow window of pH and specific conductance of the milk-derived feed, which surprisingly has proven to provide a very efficient isolation of osteopontin from chemically complex feeds.

BACKGROUND

Osteopontin is an acidic, highly phosphorylated, sialic acid rich, calcium binding protein. Osteopontin contains approx. 28 moles of bound phosphate per mol osteopontin and binds approx. 50 moles of Ca per mole osteopontin.

Osteopontin (OPN) is a multifunctional bioactive protein that is implicated in numerous biological processes, such as bone remodelling, inhibition of ectopic calcification, and cellular adhesion and migration, as well as several immune functions. Osteopontin has cytokine-like properties and is a key factor in the initiation of T helper 1 immune responses. Osteopontin is present in most tissues and body fluids, with the highest concentrations being found in milk. Supporting an inhibitory function of OPN in ectopic calcification, an in vivo model using OPN-deficient mice showed diminished calcification upon exogenous addition of the protein. In addition, OPN is involved in the urinary tract's defence against the formation of renal stones because OPN can inhibit growth and aggregation of calcium oxalate monohydrate crystals.

The biological role of OPN in milk is not clear; however, several functions could be hypothesized. Osteopontin has been reported to be involved in mammary gland development and differentiation, and high levels of OPN expression have been observed in the mammary gland in early lactation. Furthermore, the highly anionic nature of the protein could enable OPN to form soluble complexes with calcium ions and thereby inhibit unintentional calcium crystallization and precipitation in milk.

In the scientific literature osteopontin is typically purified from bone or milk and it is typically present in bovine milk in a concentration of 20 mg/L. In milk, osteopontin is a serum protein but may also to some extent associate with the casein micelles depending on the $Ca^{2+}$ level. Acid whey is the preferred raw material for industrial production of osteopontin. When acid whey is formed osteopontin is thought to leave the casein micelles as $Ca^{2+}$ leaks out into the serum phase. This aspect makes acid whey a straightforward source of osteopontin. For the same reason sweet whey has a slightly lower osteopontin content. Furthermore, sweet whey contains caseino macropeptide (CMP) from enzymatic cleavage of the kappa-casein. CMP has many biochemical resemblances with osteopontin—both are small, flexible, acidic, phosphorylated glycoproteins. For this reason CMP and osteopontin is believed to be quite similar in their binding to ion exchange resins, which will pose a problem in purifying osteopontin from a CMP-containing raw material. Another aspect is the likely degradation of osteopontin by proteolytic enzymes used for cheese making. These three aspects may have resulted in avoidance of this raw material for osteopontin purification, both for industrial production and for scientific research.

PRIOR ART

WO 02/28413 A1 describes a method of producing an osteopontin-containing composition from feedstocks, such as milk and acid whey, by means of low pH anion exchange. In WO 02/28413 A1 it is emphasised that neither the process feedstock nor the resulting product may contain cGMP, which is a type of CMP which is known to bind to anion exchangers and which would inhibit the binding of osteopontin.

WO 01/149741 A2 describes a process wherein osteopontin is purified from a milk material by mixing the milk material with soluble calcium and adjusting the pH of the mixture to selectively precipitate the other protein components of whey while keeping osteopontin in solution.

SUMMARY OF THE INVENTION

The present inventors have discovered that, surprisingly and contrary to the prejudices found in the prior art, osteopontin can be isolated by anion exchange in high yield and high purity from complex milk-derived feeds despite the presence of competing proteins of the feed. The present inventors have found that the specific conductance of the feed is particularly important for the yield and purity of osteopontin and have identified an optimum window of the specific conductance for the isolation of osteopontin from milk derived feeds.

Thus, an aspect of the invention relates to a method for isolating osteopontin from a milk-derived feed, the method comprising the steps of:
a) providing a milk-derived feed comprising osteopontin, said milk-derived feed having a pH in the range of pH 3.6-6.5 at 25 degrees C. and a specific conductance in the range of 4-10 mS/cm at 25 degrees C.,
b) subjecting said milk-derived feed to anion exchange chromatography, which includes contacting the milk-derived feed with an anion exchange medium,
c) optionally, washing the anion exchange medium, and
d) recovering the protein bound to the anion exchange medium, thereby obtaining a composition comprising isolated osteopontin.

The present invention may for example relate to a method for isolating osteopontin from a milk-derived feed, the method comprising the steps of:
a) providing a milk-derived feed comprising osteopontin, said milk-derived feed having a pH in the range of pH 3.6-6.5 at 25 degrees C. and a specific conductance in the range of 4-10 mS/cm at 25 degrees C., and wherein said milk-derived feed furthermore comprises
caseino macropeptide in an amount of at least 1% (w/w) relative to the total amount of protein of the milk-derived feed, or
free alpha casein and free beta-casein, b) subjecting said milk-derived feed to anion exchange chromatography, which includes contacting the milk-derived feed with an anion exchange medium, c) optionally, washing the anion exchange medium, and d) recovering the protein bound to the anion exchange medium, thereby obtaining a composition comprising isolated osteopontin.

Thus, in some preferred embodiments of the invention the method for isolating osteopontin from a milk-derived feed comprises the steps of:

a) providing a milk-derived feed comprising osteopontin, said milk-derived feed having a pH in the range of pH 3.6-6.5 at 25 degrees C. and a specific conductance in the range of 4-10 mS/cm at 25 degrees C., and wherein said milk-derived feed furthermore comprises caseino macropeptide in an amount of at least 1% (w/w) relative to the total amount of protein of the milk-derived feed, b) subjecting said milk-derived feed to anion exchange chromatography, which includes contacting the milk-derived feed with an anion exchange medium, c) optionally, washing the anion exchange medium, and d) recovering the protein bound to the anion exchange medium, thereby obtaining a composition comprising isolated osteopontin.

In other preferred embodiments of the invention the method for isolating osteopontin from a milk-derived feed comprises the steps of:

a) providing a milk-derived feed comprising osteopontin, said milk-derived feed having a pH in the range of pH 3.6-6.5 at 25 degrees C. and a specific conductance in the range of 4-10 mS/cm at 25 degrees C., and wherein said milk-derived feed furthermore comprises free alpha casein and free beta-casein, b) subjecting said milk-derived feed to anion exchange chromatography, which includes contacting the milk-derived feed with an anion exchange medium, c) optionally, washing the anion exchange medium, and d) recovering the protein bound to the anion exchange medium, thereby obtaining a composition comprising isolated osteopontin.

In further preferred embodiments of the invention, the method for isolating osteopontin from a milk-derived feed comprises the steps of:

a) providing a milk-derived feed comprising osteopontin, said milk-derived feed having a pH in the range of pH 3.6-6.5 at 25 degrees C. and a specific conductance in the range of 4-10 mS/cm at 25 degrees C., and wherein said milk-derived feed furthermore comprises caseino macropeptide in an amount of at least 1% (w/w) relative to the total amount of protein of the milk-derived feed, and free alpha casein and free beta-casein, b) subjecting said milk-derived feed to anion exchange chromatography, which includes contacting the milk-derived feed with an anion exchange medium, c) optionally, washing the anion exchange medium, and d) recovering the protein bound to the anion exchange medium, thereby obtaining a composition comprising isolated osteopontin.

In addition to the above-mentioned advantages, the present method allows for a more cost-efficient use of the anion exchange medium, and a higher yield of osteopontin per kg anion exchange medium.

Another advantage of the present method is an improved yield of osteopontin per anion exchange cycle as demonstrated in Example 5.

The "specific conductance" (sometimes referred to as the "specific conductivity") of an aqueous solution is a measure of the ability of the solution to conduct electricity. The specific conductance may e.g. be determined by measuring the AC resistance of the solution between two electrodes and the result is typically given in the unit miliSiemens per cm (mS/cm). The measurement of specific conductance may for example be measured according to the EPA (the US Environmental Protection Agency) Method No. 120.1.

Yet an aspect of the invention relates to the osteopontin-containing composition obtained by the present method.

A further aspect of the invention pertains to an osteopontin-containing composition as such.

DETAILED DESCRIPTION OF THE INVENTION

Figure 1:
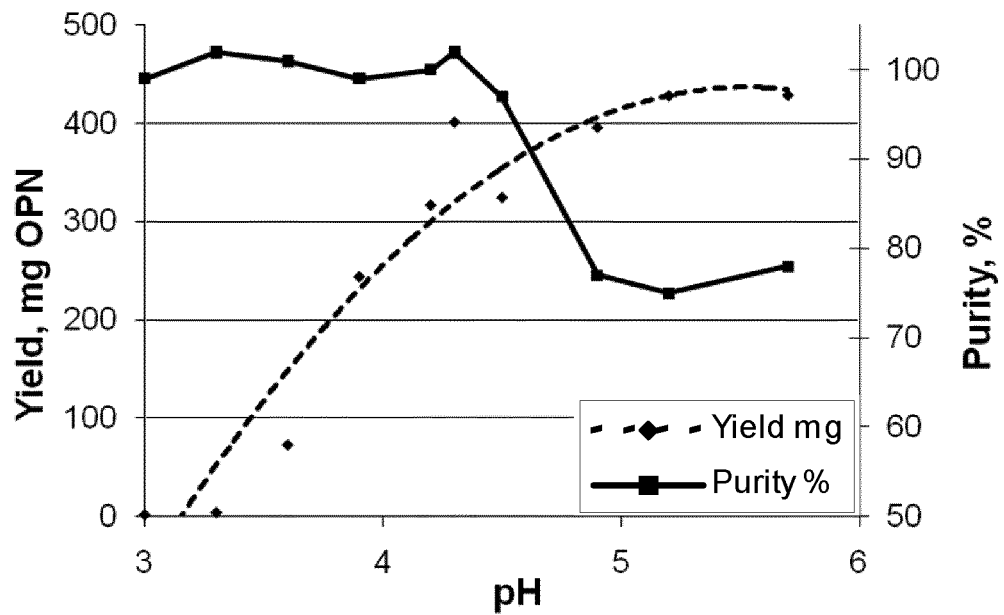
FIG. 1. The effect of pH of sweet whey-derived feed on purity and yield of osteopontin at a specific conductance of 5.5 mS/cm, FIG. 2. The effect of specific conductance of sweet whey-derived feed on purity and yield of osteopontin at pH 4.3, and FIG. 3. The influence of specific conductance of acid whey derived feed on OPN purity and yield at pH 4.3.

As mentioned, an aspect of the invention pertains to a method for isolating osteopontin from a milk-derived feed, the method comprising the steps of:

a) providing a milk-derived feed comprising osteopontin, said milk-derived feed having a pH in the range of pH 3.6-6.5 at 25 degrees C. and a specific conductance in the range of 4-10 mS/cm at 25 degrees C., and wherein said milk-derived feed furthermore comprises caseino macropeptide in an amount of at least 1% (w/w) relative to the total amount of protein of the milk-derived feed, or free alpha casein and free beta-casein, b) subjecting said milk-derived feed to anion exchange chromatography, which includes contacting the milk-derived feed with an anion exchange medium, c) optionally, washing the anion exchange medium, and d) recovering the protein bound to the anion exchange medium, thereby obtaining a composition comprising isolated osteopontin.

The steps of the method are typically performed in sequence, e.g. steps a), b), c) and d). However, in some embodiments of the invention step c) of the method is omitted and in this case the method comprises the steps a), b), and d).

In the context of the present invention the term "isolating osteopontin" relates to enrichment of osteopontin to a weight percent of at least 70% (w/w), preferably at least 80% (w/w), and even more preferably at least 90% (w/w) relative to the total weight of protein recovered from the anion exchange medium during step d). Isolating osteopontin may for example involve the enrichment of osteopontin to a weight percent of at least 95% (w/w), such as at least 97% (w/w) relative to the total weight of protein recovered from the anion exchange medium during step d).

The method is particularly useful for improving the selective enrichment of osteopontin from a milk-derived feed comprising additional protein having an isoelectric point (pI) <5.0, for example milk-derived feeds which contain CMP. The term "selective enrichment" should be understood as increasing the molar ratio between osteopontin and the total amount of other proteins of the milk-derived feed.

The isoelectric point of a protein is preferably determined by isoelectric focusing at 25 degrees C.

In the context of the present invention the term "milk-derived feed" pertains to the liquid feed which contacts the anion exchange medium.

The milk-derived feed is derived from milk from one or more mammalian source(s), e.g. milk from human, cow, sheep, goat, buffalo, camel, llama, horse and/or deer. In some preferred embodiments of the invention the milk-derived feed is derived from bovine milk.

In the context of the present invention, the terms "milk-derived feed", "sweet whey-derived feed", "acid whey-derived feed", and "milk serum-derived feed" relate to feeds wherein at least 50% (w/w) of the total protein originates from milk, sweet whey, acid whey or milk serum, respectively. In some preferred embodiments of the invention at least 90% (w/w), and preferably substantially all, of the total protein of the milk-derived feed originates from a milk, sweet whey, acid whey or milk serum.

In the context of the present invention, the term "milk" relates to the liquid obtained from the mammary glands of mammals during lactation. The term "milk" should be interpreted broadly and covers both the raw milk, i.e. the liquid obtained directly from the mammary glands, and standardised milk products such as e.g. skimmed milk or whole milk, where the concentration of the milk fat has been reduced relative to the original raw milk.

Whey is a collective term referring to the watery by-product which is produced during the manufacture of cheese or casein from milk.

In the context of the present invention, the term "sweet whey" relates to whey, which is obtained during rennet-based coagulation of milk, which for example takes place during the production of yellow cheese.

In the context of the present invention, the term "acid whey" relates to whey, which is obtained during chemical or biological acidification of milk, which for example takes place during the production of cottage cheese or quark, or in the production of casein/caseinates.

In the context of the present invention, the term "milk serum", which also is known as "serum whey", "native whey" or "lactoserum", pertains to milk from which milk fat and casein micelles have been removed. However, milk serum typically contains some free casein species, which have dissociated from the native casein micelles before the micelles were removed. Milk serum may for example be produced by microfiltering a skimmed milk through a filter or membrane having a pore size of approx. 0.1 micrometer and collecting the resulting permeate as the milk serum. Milk serum may be produced according to Evans et al.

As will be understood, the milk, sweet whey, acid whey or milk serum may have been subjected to several process steps to prepare the milk-derived feed.

Processing of milk or milk-related products typically involves one or more heat treatment processes, such as a pasteurisation (e.g. 72 degrees C. for 15 sec) or a high pasteurisation (e.g. 85 degrees C. for 20 sec).

Alternatively, or additionally, the processing may involve one or more filtration step(s). Microfiltration may be used to remove microorganisms, or alternatively to concentrate casein. Ultrafiltration or nanofiltration may e.g. be used to concentrate whey protein or milk serum protein.

Alternatively, or additionally, the processing may involve one or more centrifugation step(s), e.g. for separating fat from skimmed milk and/or separating microorganisms from the milk.

Alternatively, or additionally, the processing may involve one or more evaporation step(s) for removing water and thus concentrating dry matter such at proteins and/or minerals.

The processing may also comprise one or more pH adjustment(s). Acidification may e.g. be used to coagulate casein and pH adjustment may furthermore be important when the processing involves ion exchange chromatography.

In some embodiments of the invention the milk-derived feed comprises one more process stream(s) from the production of other milk protein fractions, such as filtered, heat treated whey or alpha-lactalbumin- and/or beta-lactoglobulin-depleted whey.

In some preferred embodiments of the invention the milk-derived feed comprises, or even essentially consists of, a milk serum-derived feed. The milk-derived feed may for example be a milk serum, and preferably a milk serum protein concentrate, e.g. in the form of the retentate obtained by ultrafiltering milk serum.

The content of osteopontin in the milk-derived feed depends on the specific feed type. In some embodiments of the invention the milk-derived feed comprises osteopontin in an amount in the range of 0.01-20% (w/w) relative to the total amount of protein of the milk-derived feed. For example, the milk-derived feed may comprise osteopontin in an amount in the range of 0.05-5% (w/w) relative to the total amount of protein of the milk-derived feed. The milk-derived feed may e.g. comprise osteopontin in an amount in the range of 0.1-2% (w/w).

Alternatively, the milk-derived feed may comprise osteopontin in an amount in the range of 0.1-1% (w/w) relative to the total amount of protein of the milk-derived feed.

In the context of the present invention, a product, component, method, or method step which is stated to "essentially consist of" one or more sub-components or one or more activities consists of the one or more specifically mentioned sub-components or the one or more specifically mentioned activities but may also include one or more additional unnamed sub-components or activities which do not materially affect the basic and novel characteristic(s) of the present invention.

As mentioned above, the present method is particularly effective for isolating osteopontin from complex feeds, i.e. feeds which contain molecular entities that interfere with the isolation of osteopontin, such as proteins having a pI lower than 5.0. Such proteins have been found to compete with osteopontin for the functional groups of the anion exchange medium.

Examples of proteins having a pI<5.0 are alpha lactalbumin, proteose peptone-3, proteose peptone-5, and proteose peptone-8, and casein-derived peptides such as caseino macropeptide and/or caseino phosphopeptides. Thus the additional protein may comprise one or more proteins from the group consisting of alpha lactalbumin, proteose peptone-3, proteose peptone-5, and proteose peptone-8, casein-derived peptide, caseino macropeptide, caseino phosphopeptide, and combinations thereof. Free alpha-casein and free beta-casein are other example of proteins having a pI value<5.0.

In some embodiments of the invention the milk-derived feed comprises an amount of additional protein having a pI<5.0 of at least 0.1% (w/w) relative to the total amount of protein of the milk-derived feed. For example, the milk-derived feed may comprise an amount of additional protein having a pI<5.0 of at least 0.5% (w/w) relative to the total amount of protein of the milk-derived feed.

Alternatively, the milk-derived feed may comprise an amount of additional protein having a pI<5.0 of at least 2% (w/w) relative to the total amount of protein of the milk-derived feed. As will be understood, the additional protein having a pI<5.0 does not include osteopontin but typically includes one or more other proteins having a pI in the specified range.

In other embodiments of the invention the milk-derived feed comprise an amount of additional protein having a pI<5.0 in the range of 0.1-50% (w/w) relative to the total amount of protein of the milk-derived feed. For example, the milk-derived feed may comprise an amount of additional protein having a pI<5.0 in the range of 0.5-40% (w/w) relative to the total amount of protein of the milk-derived feed. Alternatively, the milk-derived feed may comprise an amount of additional protein having a pI<5.0 in the range of 2-25% (w/w) relative to the total amount of protein of the milk-derived feed.

The milk-derived feed may e.g. comprise an amount of additional protein having a pI<5.0 in the range of 0.1-20% (w/w) relative to the total amount of protein of the milk-derived feed. For example, the milk-derived feed may comprise an amount of additional protein having a pI<5.0 in the range of 0.3-15% (w/w) relative to the total amount of protein of the milk-derived feed. Alternatively, the milk-derived feed may comprise an amount of additional protein having a pI<5.0 in the range of 0.5-10% (w/w) relative to the total amount of protein of the milk-derived feed.

In further embodiments of the invention the milk-derived feed comprises an amount of additional protein having a pI<5.0 in the range of 1-50% (w/w) relative to the total amount of protein of the milk-derived feed. For example, the milk-derived feed may comprise an amount of additional protein having a pI<5.0 in the range of 10-45% (w/w) relative to the total amount of protein of the milk-derived feed. Alternatively, the milk-derived feed may comprise an amount of additional protein having a pI<5.0 in the range of 15-40% (w/w) relative to the total amount of protein of the milk-derived feed.

In some preferred embodiments of the invention, the additional protein having a pI<5.0 has a pI<4.5, and preferably a pI<4.0.

In the context of the present invention the term "protein" encompasses both large aggregates of polypeptides, single polypeptide chains and peptides such as di- or tri-peptides. Chemically, proteins are polymers comprising different and/or identical amino acids linked by so-called peptide bonds.

In some preferred embodiments of the invention the milk-derived feed furthermore comprises caseino macropeptide (CMP).

In the context of the present invention, the term "CMP" or "caseino macropeptide" pertains to a small protein, which is released from kappa-casein upon exposure to rennet enzymes. CMP encompasses both glycosylated variants and a non-glycosylated variant of the protein. The glycosylated variants of the protein is sometimes referred to as caseino glycomacropeptide (cGMP).

In other preferred embodiments of the invention the milk-derived feed comprises, or even essentially consists of, sweet whey-derived feed. The milk-derived feed may for example be sweet whey, and preferably sweet whey protein concentrate, e.g. in the form of the retentate obtained by ultrafiltration of sweet whey.

In some embodiments of the invention the milk-derived feed may comprise, or even essentially consists of, an acid whey-derived feed. The milk-derived feed may for example be an acid whey, and preferably an acid whey protein concentrate, e.g. in the form of the retentate obtained by ultrafiltration of acid whey.

In the context of the present invention, the terms "milk serum protein concentrate", "sweet whey protein concentrate", or "acid whey protein concentrate" pertains to an aqueous composition which contains at least 80% (w/w) of the total protein which was present in original milk serum, sweet whey, or acid whey, respectively, and which has a total protein content of at least 25% (w/w) relative to the dry weight of the aqueous composition.

However, in other embodiments of the invention the milk-derived feed is not an acid whey-derived feed.

In preferred embodiments of the invention the milk-derived feed, e.g. a sweet whey-derived feed, comprises CMP in an amount of at least 1% (w/w) relative to the total amount of protein of the milk-derived feed. For example, the milk-derived feed, e.g. a sweet whey-derived feed, may comprise CMP in an amount of at least 5% (w/w) relative to the total amount of protein of the milk-derived feed, preferably at least 10% (w/w), and even more preferably at least 15% (w/w) relative to the total amount of protein of the milk-derived feed.

In some embodiments of the invention the milk-derived feed, e.g. a sweet whey-derived feed, comprises CMP in an amount in the range of 1-40% (w/w) relative to the total amount of protein of the milk-derived feed. For example, the milk-derived feed, e.g. a sweet whey-derived feed, may comprise CMP in an amount in the range of 5-35% (w/w) relative to the total amount of protein of the milk-derived feed, preferably in the range of 10-30% (w/w), and even more preferably in the range of 15-25% (w/w) relative to the total amount of protein of the milk-derived feed.

The present inventors have observed that, surprisingly, a precipitate is formed during the present process when the feed is based on milk serum or a concentrate thereof. The precipitate causes problems during the anion exchange process and reduces its robustness.

The inventors have investigated the precipitate and found indications that it contains precipitated casein species, which were present in dissolved form such as free beta-casein or free alpha-casein.

In the context of the present invention, the terms "free beta-casein" or "free alpha-casein" pertains beta-casein molecules or alpha-casein molecules which are not bound to the native casein micelles of milk products. Such free beta-casein or free alpha-casein includes dissolved single molecules of beta-casein or alpha-casein or small aggregates of alpha-casein and/or beta-casein. Single molecules of beta-casein are for example known to form small beta-casein micelles, which also is an example of free beta-casein.

Thus, in some preferred embodiments of the invention the milk-derived feed furthermore comprises free alpha-casein and free beta-casein. Free alpha-casein and free beta-casein are typically present in milk-serum derived feed.

The inventors have found that this precipitation problem can be solved by removing the precipitate from the milk derived feeds prior to anion exchange. Thus, in some preferred embodiments of the invention step a) of the method involves removing precipitate from the acidified liquid which is to form the milk-derived feed. Such removal may e.g. involve centrifugation or filtration of the acidified liquid.

Another solution to the precipitate problem is to use a pH of the feed where precipitation is limited or even absent, e.g. in the range of pH 5.0-6.5.

The milk-derived feed may therefore have a pH in the range of 5.0-6.5, and preferably in the range of pH 5.0-6.0.

When performing the anion exchange in this pH range it is furthermore suggested to use a feed/process temperature above 15 degrees C., such as 20-40 degrees C. In this temperature range dissolved beta-casein forms small beta-casein micelles, not to be confused with native casein micelles of milk, and these beta-casein micelles seem to interfere less with the anion exchange process than single beta-casein molecules.

The temperature of the milk-derived feed and anion exchange material during step b) may therefore be in the range of 15-40 degrees C., and preferably in the range of 20-38 degrees C.

The milk-derived feed may e.g. comprise a total amount of free alpha-casein and free beta-casein of at least 0.5% (w/w) relative to the total amount of protein of the milk-derived feed. For example, the milk-derived feed may comprise a total amount of free alpha-casein and free beta-casein of at least 2% (w/w) relative to the total amount of protein of the milk-derived feed. The milk-derived feed may e.g. comprise a total amount of free alpha-casein and free beta-casein of at least 10% (w/w) relative to the total amount of protein of the milk-derived feed.

In some embodiments of the invention the milk-derived feed comprises a total amount of free alpha-casein and free beta-casein in an amount in the range of 0.5-40% (w/w) relative to the total amount of protein of the milk-derived feed. For example, the milk-derived feed may comprise a total amount of free alpha-casein and free beta-casein in an amount in the range of 2-20% (w/w) relative to the total amount of protein of the milk-derived feed. The milk-derived feed may e.g. comprise a total amount of free alpha-casein and free beta-casein in an amount in the range of 5-15% (w/w) relative to the total amount of protein of the milk-derived feed.

In some embodiments of the invention the milk-derived feed comprises alpha-lactalbumin in an amount of at least 1% (w/w) relative to the total amount of protein of the milk-derived feed. For example, the milk-derived feed may comprise alpha-lactalbumin in an amount of at least 10% (w/w) relative to the total amount of protein of the milk-derived feed, preferably at least 20% (w/w), and even more preferably at least 30% (w/w) relative to the total amount of protein of the milk-derived feed.

In some embodiments of the invention the milk-derived feed comprises alpha-lactalbumin in an amount in the range of 1-50% (w/w) relative to the total amount of protein of the milk-derived feed. For example, the milk-derived feed may comprise alpha-lactalbumin in an amount in the range of 5-40% (w/w) relative to the total amount of protein of the milk-derived feed, preferably in the range of 10-35% (w/w), and even more preferably in the range of 12-30% (w/w) relative to the total amount of protein of the milk-derived feed.

In some embodiments of the invention the milk-derived feed comprises beta-lactoglobulin in an amount of at least 1% (w/w) relative to the total amount of protein of the milk-derived feed. For example, the milk-derived feed may comprise beta-lactoglobulin in an amount of at least 15% (w/w) relative to the total amount of protein of the milk-derived feed, preferably at least 30% (w/w), and even more preferably at least 40% (w/w) relative to the total amount of protein of the milk-derived feed.

In some embodiments of the invention the milk-derived feed comprises beta-lactoglobulin in an amount in the range of 1-70% (w/w) relative to the total amount of protein of the milk-derived feed. For example, the milk-derived feed may comprise beta-lactoglobulin in an amount in the range of 10-65% (w/w) relative to the total amount of protein of the milk-derived feed, preferably in the range of 20-60% (w/w), and even more preferably in the range of 35-55% (w/w) relative to the total amount of protein of the milk-derived feed.

Caseins are known to precipitate at pH-values at or below about 4.6. In some embodiments of the invention it is therefore preferred that milk-derived feed having a pH in the range of about 3.6-4.6 has a relatively low concentration of casein, such as at most 1% (w/w) relative to the total amount of protein of the milk-derived feed.

In some embodiments of the invention the milk-derived feed comprises at most 0.1% casein (w/w) relative to the total amount of protein of the milk-derived feed. It may even be preferred that the milk-derived feed comprises at most 0.01% casein (w/w) relative to the total amount of protein of the milk-derived feed.

In some preferred embodiments of the invention the milk-derived feed comprises a total amount of protein in the range of 6-250 g/L milk-derived feed. For example, the milk-derived feed may comprise a total amount of protein in the range of 50-150 g/L milk-derived feed. It may even be preferred that the milk-derived feed comprises a total amount of protein in the range of 75-125 g/L milk-derived feed.

Alternatively, the milk-derived feed may comprise a total amount of protein in the range of 50-250 g/L milk-derived feed. For example, the milk-derived feed may comprise a total amount of protein in the range of 50-150 g/L milk-derived feed. It may even be preferred that the milk-derived feed comprises a total amount of protein in the range of 75-150 g/L milk-derived feed.

It may also be preferred that the milk-derived feed may comprise a total amount of protein in the range of 75-250 g/L milk-derived feed.

In some preferred embodiments of the invention the milk-derived feed comprises a total amount of protein of at least 6 g/L milk-derived feed. For example, the milk-derived feed may comprise a total amount of protein of at least 50 g/L milk-derived feed. It may even be preferred that the milk-derived feed comprises a total amount of protein of at least 75 g/L milk-derived feed.

In some preferred embodiments of the invention the milk-derived feed has a pH in the range of pH 3.8-6.0 at 25 degrees C. Preferably, the pH of the milk-derived feed at 25 degrees C. is in the range of pH 4.0-5.5. Even more preferably, the pH of the milk-derived feed at 25 degrees C. is in the range of pH 4.2-5.0, such as e.g. pH 4.3-4.5.

The desired specific conductance of the milk-derived feed may for example be obtained by:
  concentrating the milk-derived feed by partial removal of water and/or addition of salt(s), which results in an increased specific conductance, or
  desalting the milk-derived feed by removal of salt(s) and/or addition of water, which results in a reduced specific conductance.

Techniques for removing water and/or salt(s) from an aqueous liquid are well-known to the person skilled in the art.

In some preferred embodiments of the invention the milk-derived feed has a specific conductance in the range of 4.5-9.0 mS/cm at 25 degrees C. For example, the specific conductance of the milk-derived feed may be in the range of 5.0-8.0 mS/cm at 25 degrees C. In some preferred embodiments of the invention it may be even more preferable that the specific conductance of the milk-derived feed is in the range of 5.5-7.0 mS/cm at 25 degrees C.

The milk-derived feed may for example have a specific conductance in the range of 4-7 mS/cm at 25 degrees C. Alternatively, the milk-derived feed may have a specific conductance in the range of 7-10 mS/cm at 25 degrees C. Alternatively, the milk-derived feed may have a specific conductance in the range of 5-8 mS/cm at 25 degrees C.

In some preferred embodiments of the invention the milk-derived feed has a specific conductance in the range of 4-7 mS/cm at 25 degrees C. and a pH in the range of pH 3.6-5.0 at 25 degrees C.

In other preferred embodiments of the invention the milk-derived feed has a specific conductance in the range of 7-10 mS/cm at 25 degrees C. and a pH in the range of pH 5.0-6.5 at 25 degrees C.

In further preferred embodiments of the invention the milk-derived feed has a specific conductance in the range of 5-8 mS/cm at 25 degrees C. and a pH in the range of pH 4.0-5.5 at 25 degrees C.

For example, the milk-derived feed may have a specific conductance in the range of 5-6 mS/cm at 25 degrees C. and a pH in the range of pH 4.2-5.0 at 25 degrees C.

In some embodiments of the invention, the milk-derived feed has a pH in the range of 3.6 to 6.5 and
if the pH is in the range of 3.6-5.0, the specific conductance is
at least 4 mS/cm and
at most $cond._{max}$=1.38 mS/cm*pH+1.03 mS/cm, and
if the pH is in the range of 5-6.5, the specific conductance is
at least $cond._{min}$=1.33 mS/cm*pH−2.67 mS/cm, and
at most $cond._{max}$=1.38 mS/cm*pH+1.03 mS/cm.

Thus, if the pH of a feed of these embodiments is e.g. pH 6.0 the specific conductance is
at least $cond._{min}$=1.33 mS/cm*6.0-2.67 mS/cm=5.3 mS/cm, and
at most $cond._{max}$=1.38 mS/cm*6.0+1.03 mS/cm=9.3 mS/cm.

For example, the milk-derived feed may have a pH in the range of 3.6 to 5.0 and a specific conductance of
at least 4 mS/cm and
at most $cond._{max}$=1.38 mS/cm*pH+1.03 mS/cm.

Alternatively, the milk-derived feed may have a pH in the range of 5.0 to 6.5 and a specific conductance of
at least at least $cond._{min}$=1.33 mS/cm*pH−2.67 mS/cm and
at most $cond._{max}$=1.38 mS/cm*pH+1.03 mS/cm.

Specific conductivities and pH-values are measured in feeds having a temperature of 25 degrees C. unless it is stated otherwise.

In some embodiments of the invention the anion exchange medium comprises a solid phase and one or more cationic groups.

Preferably, at least some of the cationic groups are attached to the surface of the solid phase and/or to the surface of pores which are accessible through the surface of the solid phase.

In some embodiments of the invention the solid phase of the anion exchange medium comprises one or more components selected from the group consisting of a plurality of particles, a filter, and a membrane.

The solid phase may for example comprise, or even essentially consists of, polysaccharide. Cross-linked polysaccharides are particularly preferred. Examples of useful polysaccharides are cellulose, agarose, and/or dextran.

Alternatively, the solid phase may comprise, or even essentially consists of, a non-carbohydrate polymer. Examples of useful non-carbohydrate polymers are methacrylate, polystyrene, and/or styrene-divinylbenzene.

In some preferred embodiments of the invention the cationic groups comprises, or even essentially consists of, amino groups. Tertiary amino groups are particularly preferred and result in quaternary ammonium groups under appropriate pH conditions. Quaternary ammonium groups provide strong anion exchange characteristics to the anion exchange medium.

Alternatively, or additionally, the cationic groups may comprise one or more primary or secondary amino groups. A substantial amount of primary or secondary amino groups typically provides the anion exchange medium with weak anion exchange characteristics.

The optimal protein load per cycle depends on the design of the anion exchange chromatography system and the characteristics of the anion exchange medium.

The process conditions during the anion exchange chromatography, including pressure, flow rate, etc., depend on the actual process implementation, the used equipment and the used anion exchange medium.

The temperature of the milk-derived feed during step b) is typically sufficiently low to avoid microbial growth and heat damaging of the protein and the anion exchange medium but sufficiently high to provide an acceptable viscosity.

In some embodiments of the invention the temperature of the milk-derived feed during step b) is in the range of 2-40 degrees C. Preferably, the temperature of the milk-derived feed during step b) is in the range of 4-20 degrees C., and even more preferably in the range of 6-12 degrees C.

More details regarding anion exchange chromatography and its industrial implementation can be found in Scopes, which is incorporated herein by reference for all purposes.

In some preferred embodiments of the invention the method of the invention comprises a step c) of washing the anion exchange medium with a washing solution after contacting it with the milk-derived feed. Useful washing solutions are typically pH neutral or weak acidic aqueous solutions capable of removing loosely bound molecules from the anion exchange medium. One may for example use demineralised water or a pH neutral aqueous solution of sodium chloride, e.g. 0.1 M NaCl, as washing liquid.

In other preferred embodiments of the invention, the method of the present invention does not contain step c).

Step d) of the present invention involves recovering the osteopontin bound to the anion exchange medium. The recovery is typically performed by contacting the anion exchange medium with an eluent and collecting the resulting eluate, i.e. the eluent plus the molecules released from the anion exchange medium.

Normally, the eluent is an aqueous solution having an ion strength and/or pH sufficient to release bound osteopontin from the anion exchange medium. Examples of useful eluents are pH-neutral, 1.0 M aqueous solutions of salts such as NaCl, $CaCl_2$, KCl, $MgCl_2$, or a combination thereof.

The recovered composition may be subjected to additional process steps e.g. for demineralising and concentrating the composition, and subsequently transforming it into a powder.

Thus, in some preferred embodiments of the invention, the recovered composition is furthermore subjected to one or more of the process step(s) selected from the group consisting of concentration, diafiltration, evaporation of solvent, spray-drying, and substitution of protein-bound cations.

For example, the recovered composition may be subjected to a concentration step.

Alternatively, or in addition, the recovered composition may be subjected to a diafiltration step.

Alternatively, or in addition, the recovered composition may be subjected to an evaporation step.

Alternatively, or in addition, the recovered composition may be subjected to a spray-drying step.

In a preferred embodiment of the invention the recovered composition is subjected to the following steps:
  i) concentrating, e.g. by ultrafiltration,
  ii) diafiltration, e.g. against water,
  iii) optionally, another concentration step, e.g. by evaporation,
  iv) cation replacement by contacting the aqueous composition of step ii) or iii) with a water soluble calcium salt, e.g. $CaCl_2$,
  v) pasteurisation, and
  vi) spray-drying to convert the pasteurised composition into a powder.

The present method may both be implemented as a batch process or a semi-batch-process. The semi-batch process may for example be implemented by operating a first and a second anion exchange column, and performing step b) on the first anion exchange column while performing steps c) and/or d) on the second anion exchange column, and vice versa.

Thus, in some preferred embodiments of the invention the method for isolating osteopontin from a milk-derived feed comprises the steps of:
  a) providing a milk-derived feed comprising osteopontin, said milk-derived feed is a sweet whey protein concentrate, said milk-derived feed having a pH in the range of pH 3.6-6.5 at 25 degrees C. and a specific conductance in the range of 4-10 mS/cm at 25 degrees C., and wherein said milk-derived feed furthermore comprises caseino macropeptide in an amount of at least 1% (w/w) relative to the total amount of protein of the milk-derived feed,
  b) subjecting said milk-derived feed to anion exchange chromatography, which includes contacting the milk-derived feed with an anion exchange medium,
  c) optionally, washing the anion exchange medium, and
  d) recovering the protein bound to the anion exchange medium, thereby obtaining a composition comprising isolated osteopontin.

In other preferred embodiments of the invention the method for isolating osteopontin from a milk-derived feed comprises the steps of:
  a) providing a milk-derived feed comprising osteopontin, said milk feed is a milk serum protein concentrate, said milk-derived feed having a pH in the range of pH 3.6-6.5 at 25 degrees C. and a specific conductance in the range of 4-10 mS/cm at 25 degrees C., and wherein said milk-derived feed furthermore comprises free alpha casein and free beta-casein,
  b) subjecting said milk-derived feed to anion exchange chromatography, which includes contacting the milk-derived feed with an anion exchange medium,
  c) optionally, washing the anion exchange medium, and
  d) recovering the protein bound to the anion exchange medium, thereby obtaining a composition comprising isolated osteopontin.

Yet an aspect of the invention relates to an osteopontin-containing composition obtainable by the method described herein.

The present invention has been described above with reference to specific embodiments. However, other embodiments than the above described are equally possible within the scope of the invention. The different features and steps of various embodiments and aspects of the invention may be combined in other ways than those described herein unless it is stated otherwise.

EXAMPLES

Example 1

Enrichment of Osteopontin from Controlled Conductance Sweet Whey Concentrate

Protocol

The following purification experiments were conducted on Fast Protein Liquid Chromatography (FPLC) equipment equipped with the strong anion exchange resin Q-Sepharose Bigbeads packed in a 13.3 mL (170 mm×10 mm) column. The flow was maintained at 3.33 ml/min throughout the loading, wash and elution in all experiments. The raw material was a sweet whey protein isolate and 70 g of total protein was loaded on the column during each experiment. The content of CMP in the raw material was analysed. Samples of the raw material was diluted to a final protein concentration of 10% w/v, hereafter pH (pH 3.0-5.7, at 4.7 mS/cm) and specific conductance (2.3-10.3 mS/cm at pH 4.3) were adjusted by addition of HCl and NaCl, respectively. Unbound proteins were washed out of the column by 3 bed volumes of 100 mM NaCl, pH 5.0 solution. Subsequently, the bound proteins were eluted by passage of 1 M NaCl, pH 5.0 solution through the column until no more protein was detected in the eluate.

For each eluate sample, the contents of osteopontin (OPN), CMP, and total protein were analysed using the following techniques.

Determination of Total Protein

Total protein content of the eluate was measured by standard Kjeldahl digestion as described in Cohen.

OPN Quantification by HPLC Method

Analytical Principle:

The sample was filtered through a 0.22 µm filter and subjected to HPLC with column MonoQ HR 5/5 (1 ml), Pharmacia and detection at 280 nm. The concentration of the sample was calculated by the external standard method (comparison with peak area of standard with known OPN content). It is a prerequisite for this analytical procedure that the samples comprise relatively pure OPN, e.g. as determined by SDS-PAGE (Laemmli, 1970), due to the low specificity of the method.

Reagents: OPN standard, Milli Q water, HPLC grade, NaCl, Merck, Tris HCl, Sigma

Buffer A: 10 mM NaCl, 20 mM Tris HCL, pH 8.0
Buffer B: 0.8 M NaCl, 20 mM Tris HCl, pH 8.0

A standard calibration curve was made from 5 standards in the concentration range 1-10 mg/ml of OPN standard in buffer A. All standards were filtered by 0.22 µm filters before loading onto the column.

Sampling and Pretreatment:

Samples for analysis were diluted with Milli Q water, HPLC grade, if they were out of range of the standard calibration curve. Dilution was in some instances also necessary to enable binding of OPN to the anion exchange resin if much NaCl from the eluent was present. An amount equivalent to 25 µL of 1-10 mg/mL OPN was injected for analysis. Samples were filtered through 0.22 µm filters before injection to HPLC.

HPLC conditions: Flow 1 ml/min, injection volume 25 µL, gradient: 0-3 min 0% B, 3-17 min 0-60% B, 17-30 min 60-100% B, 30-33 min 100% B, 33-34 min 100-0% B, 34-40 min 0% B.

Calculation and Expression of Results:

The concentration of OPN in each sample was calculated by reference to the standard curve and by observing the employed dilutions.

The purity was calculated by the ratio between OPN and total protein, using the OPN specific Jones factor of 7.17 as most or all protein determined by Kjeldahl digestion in the current context was OPN.

Quantification of Major Whey Proteins by HPLC

Separation and quantification of major whey protein, alpha-lactalbumin, β-lactoglobulin and CMP (caseino glycomacropeptide) by gel permeation chromatography.

The gel permeation chromatography was conducted using 2 columns of TSKgel3000PWxl (7.8 mm×30 cm) connected in series with attached precolumn PWxl (6 mm 4 cm)(Tosohass, Japan).

The standard solution for calibration of the system consisted of: 225 mg CMP; 225 mg alpha-lactalbumin and 50 mg β-lactoglobulin dissolved in 500.0 ml 0.02 M phosphate buffer 7.5.

Pretreatment of samples: Powder samples were dissolved in phosphate buffer at 1 mg/ml and left over night for solubilisation. Alternatively, liquid samples were diluted with phosphate buffer to obtain a content of approx. 0.1% protein. If the protein content was below 0.1%, the sample was measured undiluted. All samples were filtered through 0.22 µm filters before injection to the column.

Calculation and Expression of Results:

Percentage of individual protein in sample was calculated according to A×0.1×F, where
B
A=area measured in sample
0.1=conversion factor for 0.1% solution
F=dilution factor (100,000/sample weight in mg)
B=calculated area of individual protein in 0.1% standard solution Results Content of CMP The content of CMP in the sweet whey raw material was 20.1%, but CMP was surprisingly undetectable in the enriched OPN compositions of Example 1.

The Effect of Feed pH on Purity and Yield of Osteopontin:

The first series of experiments with varying the pH value of the applied feed, shown in FIG. 1, show that the yield of OPN (mg OPN from 70 g total protein in the feed) increases as the pH increases from pH 3 to approx. pH 4.3. The high yield is maintained when the pH is increased beyond pH 4.3. The purity of OPN in the obtained OPN preparations is very high at low pH values, but when the pH is increased above approx. pH 4.5 the purity slowly declines but is still acceptable until approx. pH 6.5. However, the best yield of high purity OPN is obtained in the pH window pH 3.8-5.5, and particularly in the range pH 4.3-4.5.

Figure 2:
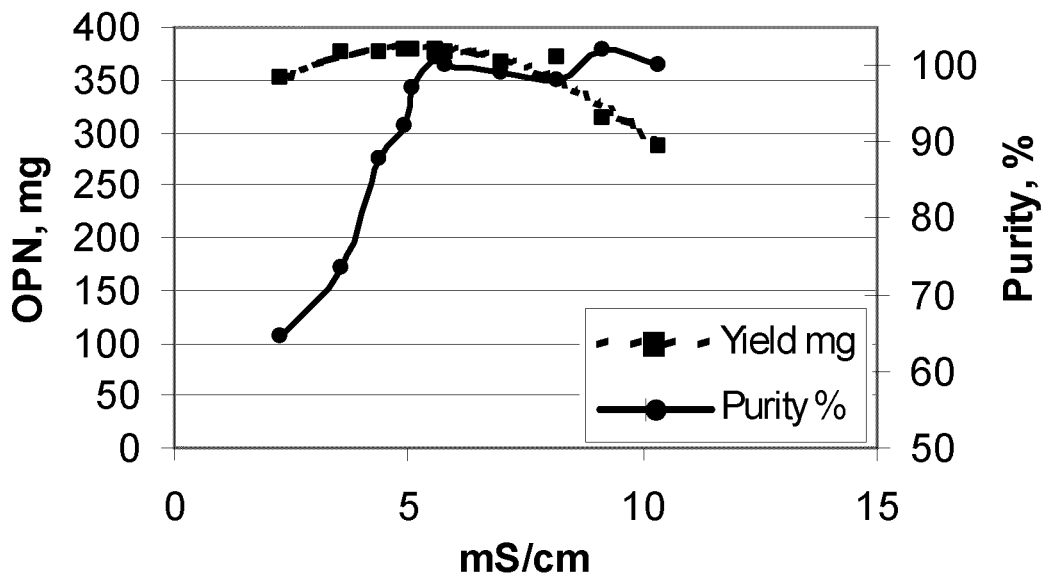

The Effect of Specific Conductance of the Feed on Purity and Yield of Osteopontin:

The results from the series of experiments with varying specific conductance are shown in FIG. 2. At low specific conductance the yield is high while the purity is low. With increasing specific conductance the purity increases and reaches 100 at approx. 5.5 mS/cm. When the specific conductance is increased further the purity remains high, whereas the yield of OPN starts to decline when the specific conductance exceeds approx. 10 mS/cm. However, the best yield of high purity OPN seems to obtained in the specific conductance range 4.5-9.0 mS/cm, and particularly in the range 5-8 mS/cm.

Discussion/Conclusion

Effect of pH:

It is seen from FIG. 1 that at a pH value below approx. pH 3.6 OPN is decreasing its charge and hence it is decreasing its binding to the cationic groups of the resin. At pH values above approx. pH 4.5 the purity of OPN starts to decrease as other proteins of the feed become negatively charged and start binding to the resin. We have thus identified a window of optimal pH values in the range pH 3.6-6.5 for isolating OPN of high purity and with high yield even though the feed contains a large amount of CMP. In the resulting OPN preparation CMP is not detectable.

Effect of Specific Conductance:

It is seen from FIG. 2 that at a specific conductance below approx. 4 mS/cm the purity of OPN is decreasing as other proteins can bind to the resin. At specific conductances above approx. 6 mS/cm the binding of OPN to the resin becomes weaker and the yield slowly decreases but is acceptable until a specific conductance of approx. 10 mS/cm. Thus, we have identified a narrow range from approx. 4-10 mS/cm to be optimal for OPN production. In this narrow range OPN can be isolated in high yield and with high purity even from a raw material which contains approx. 20% CMP.

Several additional experiments have been performed exploring the claimed pH/specific conductance window in sweet whey based-feeds and the additional experiments confirm the above-mentioned conclusions.

Example 2

Enrichment of Osteopontin from Controlled Conductance Acid Whey Concentrate

The following purification experiment was conducted on FPLC equipment similar to Example 1. The raw material, however, was acid whey concentrate having a total protein content of 10% (w/w) and approx. 70 g of total protein was loaded on the column.

The concentrated acid whey was diluted to different degrees giving rise to specific conductivities in the range from 2.5 to 10 mS/cm. OPN and total protein was measured in the feed and the eluate by the methods described in Example 1. The pH was adjusted to 4.3 by addition of HCl and the raw material applied to the anion exchange column. Unbound proteins were washed out of the column by 3 bed volumes of 0.1 M NaCl and the bound proteins were subsequently eluted by passage of 1 M NaCl solution through the column until no more protein was detected in the eluate.

Figure 3:
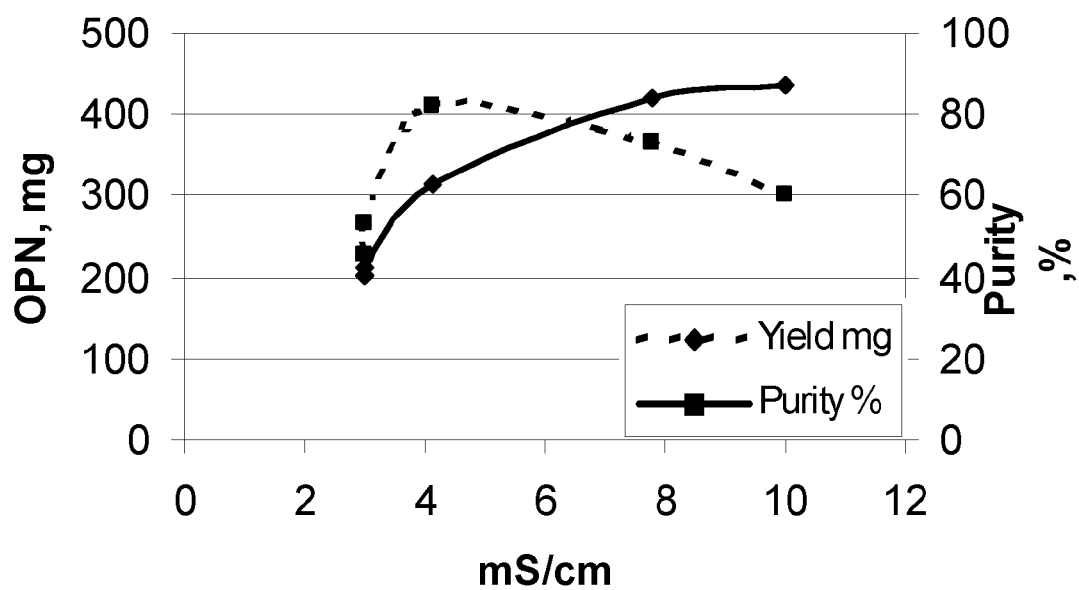

The influence of the specific conductance on OPN purity and yield during OPN enrichment from concentrated acid whey is shown in FIG. 3.

The data in FIG. 3 shows an enrichment of OPN from acid whey by the described procedure. As in Example 1 where sweet whey was used as raw material, it is again observed that low specific conductance in the feed increases the yield on the sacrifice of purity of the product. However, as acid whey derived feeds do not contain large quantities of CMP the effect is not as detrimental to the enrichment of OPN as in the case where the feed is derived from sweet whey. Acid whey derived feed does contain minor components, which binding can be minimised by the same parameter settings as employed to avoid binding of CMP. Thus, it can be observed that the narrow optimum range of OPN isolation identified in Example 1 applies to the OPN isolation from acid whey as well.

We have performed several additional experiments exploring the claimed pH/specific conductance window in acid whey based-feeds and the additional experiments confirm the above-mentioned findings.

Example 3

Enrichment of Osteopontin from Controlled Conductance Milk Serum Concentrate In accordance with the previous examples milk serum can be used as raw material for OPN production by the disclosed method. Milk serum was produced by microfiltration (filter pore size of approx. 0.1 micron) of skimmed milk at 24 degrees so as to remove micellar casein. Samples of milk serum were thereafter adjusted to pH 4.3 or pH 4.7 by HCl and diafiltered to obtain specific conductances in the range of 4-10 mS/cm and a total protein content of approx. 5% or 10% (w/w). Subsequently, OPN was enriched from the modified milk serum samples by anion exchange at approx. 5 degrees C. as described in example 1.

Results and Observations

The performed trials demonstrated that feeds derived from milk serum also may be used in the present process.

Surprisingly, unidentified precipitation was observed during the process resulting in clogging or contamination of the anion exchange material after some cycles of anion exchange. The precipitation problem was solved by filtering the acidified milk serum through filter paper prior to the anion exchange. We have seen indications that the precipitate is related to dissolved casein species, such as free alpha- and free beta-casein that stay in the milk serum when the native casein micelles are removed.

Discussion/Conclusion

Milk serum is produced by microfiltration of skimmed milk so as to remove caseins, whereas sweet and acid whey are casein depleted by precipitation of caseins by action of rennet or acid, respectively. Thereby all three categories of milk derived feeds are essentially free of micellar casein, which would interfere with anion exchange chromatographic procedures due to precipitation and flocculation of caseins.

We have seen indications that dissolved caseins cause problems during anion exchange. This problem can solved by filtering the milk derived feeds prior to anion exchange using e.g. a microfilter.

Alternatively, the anion exchange step may be performed at a pH where precipitation is limited or even absent, e.g. in the range of pH 5.0-6.5. When performing the anion exchange in this pH range it is furthermore suggested to use a feed/process temperature above 15 degrees C., such as 20-40 degrees C. In this temperature range dissolved beta-casein forms small beta-casein micelles, not to be confused with native casein micelles, and these beta-casein micelles interfere less with the anion exchange process than single beta-casein molecules.

Example 4

Enrichment of Osteopontin from Sweet Whey Concentrate Without Controlled Conductance The following purification experiment was conducted on FPLC equipment similar to Example 1. The raw material was sweet whey isolate and approx. 1 g of total protein was loaded on the column. Before loading to the column the sweet whey was concentrated by ultrafiltration, diafiltered after addition of an equal volume of water and finally diluted again by an equal volume of water. The resulting specific conductance was 2.1 mS/cm. CMP and total protein was measured in feed and eluate by the methods described in Example 1. The amount of OPN could not be measured due to interfering proteins in both feed and eluate. OPN data in Table 1 is estimated from known yields in experiments from Example 1.

The pH was adjusted to 4.3 by addition of HCl and the raw material applied to the anion exchange column. Unbound proteins were washed out of the column by 3 bed volumes of water and the bound proteins were hereafter eluted by passage of 1 M NaCl solution through the column until no more protein was detected in the eluate.

TABLE 1

Results of anion exchange of low conductance sweet whey

|  | Raw material | Eluate |
| --- | --- | --- |
| Total protein, mg | 979 | 192 |
| OPN, mg | 2.9 | 2.8 |
| Purity of OPN, % | 0.3 | 1.5 |
| GMP, mg | 193 | 186 |
| Purity GMP, % | 19.7 | 97 |

Discussion/Conclusion:

The data in Table 1 show an enrichment of acidic whey proteins by the described procedure. However, OPN is only enriched to a minor extend because it constitutes a minor fraction of acidic whey proteins in the feed. As e.g. CMP is also binding to the resin and is present in the feed in a high concentration this protein takes up a large amount of the binding capacity of the resin. Therefore this procedure is not satisfactory for OPN production.

Example 5

Comparison and Conclusion (Comparing Example 1 with Example 4)

Some characteristics of the processes in Examples 1 and 4 are compared in Table 2 below.

TABLE 2

Characteristics of Example 1 and 4

|  | Example 1 | Example 4 |
| --- | --- | --- |
| pH | 4.3 | 4.3 |
| Specific conductance, mS/cm | 6.0 | 2.1 |
| Protein load pr. ml resin, g/ml | 5.26 | 0.074 |
| Estimated OPN of protein in raw material, % | 0.3 | 0.3 |
| Fold enrichment of OPN | 333 | 5 |
| Purity of OPN in eluate, % | 100 | 1.5 |

CONCLUSION

As summarized in Table 2, the method of Example 1 is much more specific for enriching OPN than the method of Example 4. Thus, much more protein can be loaded to the column per cycle and the yield of OPN per cycle is much higher with the method of Example 1. This method results in practically pure OPN, whereas CMP dominates the product of Example 4.

REFERENCES

Cohen Julius B. Cohen, *Practical Organic Chemistry*, 1910
Evans et al. Evans et al., "Comparison of composition, sensory, and volatile components of thirty-four percent whey protein and milk serum protein concentrates", J. Dairy Sci. 92:4773-4791, 2009
Scopes Protein Purification: Principles and Practice; Robert K. Scopes; 3rd edition, Springer Verlag New York, Inc., ISBN 0-387-94072-3

WO 02/28413 A1
WO 01/149741 A2
WO 99/33415 A1

The invention claimed is:

1. A method for isolating osteopontin from a milk-derived feed, the method comprising the steps of:
   a) providing a milk-derived feed comprising osteopontin, said milk-derived feed having a pH in the range of pH 3.6-6.5 at 25 degrees C. and a specific conductance in the range of 4-10 mS/cm at 25 degrees C.,
   and wherein said milk-derived feed furthermore comprises casein macropeptide in an amount of at least 1% (w/w) relative to the total amount of protein of the milk-derived feed,
   b) subjecting said milk-derived feed to anion exchange chromatography, which includes contacting the milk-derived feed with an anion exchange medium,
   c) optionally, washing the anion exchange medium, and
   d) recovering the protein bound to the anion exchange medium, thereby obtaining a composition comprising isolated osteopontin.

2. The method according to claim 1, wherein the milk-derived feed comprises CMP in an amount of at least 5% (w/w).

3. The method according to claim 1, wherein the milk-derived feed furthermore comprises additional protein having an isoelectric point (pI)<5.0.

4. The method according to claim 3, wherein the one or more additional protein(s) comprises one or more protein(s) selected from the group consisting of alpha lactalbumin, caseino macropeptide, caseino phosphopeptide, proteose peptone-3, proteose peptone-5, proteose peptone-8, and a mixture thereof.

5. The method according to claim 1, wherein the milk-derived feed comprises a milk serum-derived feed.

6. The method according to claim 1, wherein the milk-derived feed comprises a sweet whey-derived feed.

7. The method according to claim 1, wherein the milk-derived feed comprises CMP in an amount in the range of 1-40% (w/w) relative to the total amount of protein of the milk-derived feed.

8. The method according to claim 1, wherein the milk-derived feed comprises at total amount of free alpha casein and free beta-casein in an amount of at least 0.5% (w/w) relative to the total amount of protein of the milk-derived feed.

9. The method according to claim 8, wherein the milk-derived feed has a pH in the range of 5.0-6.5.

10. The method according to claim 8, wherein the milk-derived feed has a temperature in the range of 15-40 degrees C.

11. The method according to claim 1, wherein step a) of providing the milk-derived feed involves removing precipitate from an acidified liquid which is to form the milk-derived feed.

12. The method according to claim 1, wherein the milk-derived feed comprises alpha-lactalbumin in an amount of at least 1% (w/w) relative to the total amount of protein of the milk-derived feed.

13. The method according to claim 1, wherein the milk-derived feed comprises alpha-lactalbumin in an amount in the range of 1-50% (w/w) relative to the total amount of protein of the milk-derived feed.

14. The method according to claim 1, wherein the milk-derived feed comprises beta-lactoglobulin in an amount of at least 1% (w/w) relative to the total amount of protein of the milk-derived feed.

15. The method according to claim 1, wherein the milk-derived feed comprises beta-lactoglobulin in an amount in the range of 1-70% (w/w) relative to the total amount of protein of the milk-derived feed.

16. The method according to claim 1, wherein the milk-derived feed comprises a total amount of protein in the range of 6-250 g/L milk-derived feed.

17. The method according to claim 1, wherein the milk-derived feed has a pH in the range of pH 3.8-5.5 at 25 degrees C.

18. The method according to claim 1, wherein the milk-derived feed has a specific conductance in the range of 4.5-9.0 mS/cm at 25 degrees C.

19. The method according to claim 1, wherein the milk-derived feed has a specific conductance in the range of 4-7 mS/cm at 25 degrees C.

20. The method according to claim 1, wherein the milk-derived feed has a specific conductance in the range of 5-8 mS/cm at 25 degrees C.

21. The method according to claim 1, wherein the milk-derived feed has a specific conductance in the range of 7-10 mS/cm at 25 degrees C.

22. The method according to claim 1, wherein the anion exchange medium comprises a solid phase and one or more cationic groups.

23. The method according to claim 22, wherein the solid phase of the anion exchange medium comprises one or more components selected from the group consisting of a plurality of particles, a filter, and a membrane.

24. The method according to claim 22, wherein the solid phase comprises polysaccharide.

25. The method according to 22, wherein the solid phase comprises cross-linked polysaccharide.

26. The method according to 22, wherein the solid phase comprises sepharose.

27. The method according to 22, wherein the cationic groups comprise amino groups.

28. The method according to 1, wherein the recovered composition furthermore is subjected to one or more of the process step(s) selected from the group consisting of concentration, diafiltration, evaporation of solvent, spray-drying, and substitution of protein-bound cations.

29. The method according to claim 1, wherein the isolated osteopontin comprises at least 70% (w/w) relative to total weight of protein recovered from the anion exchange medium.

* * * * *